(12) United States Patent
Gábor

(10) Patent No.: US 7,141,604 B2
(45) Date of Patent: Nov. 28, 2006

(54) CITALOPRAM FOR THE TREATMENT OF ELEVATED BLOOD PRESSURE

(75) Inventor: Pál S. Gábor, Budapest (HU)

(73) Assignee: Egis Gyógyszergyár Rt., Budapest (HU)

( * ) Notice: Subject to any disclaimer, the term of this patent is extended or adjusted under 35 U.S.C. 154(b) by 0 days.

(21) Appl. No.: 10/489,179

(22) PCT Filed: Mar. 13, 2003

(86) PCT No.: PCT/HU03/00021

§ 371 (c)(1),
(2), (4) Date: Nov. 15, 2004

(87) PCT Pub. No.: WO03/075914

PCT Pub. Date: Sep. 18, 2003

(65) Prior Publication Data

US 2005/0065209 A1    Mar. 24, 2005

(30) Foreign Application Priority Data

Mar. 14, 2002  (HU) ................................. 0200980

(51) Int. Cl.
*A61K 31/34*    (2006.01)
(52) U.S. Cl. ..................................... 514/469
(58) Field of Classification Search ............... 514/218, 514/255.03, 266.2, 266.5, 415, 470, 603, 514/652, 653
See application file for complete search history.

(56) References Cited

U.S. PATENT DOCUMENTS 6,229,026 B1 *  5/2001  Petersen ..................... 549/467
6,333,357 B1 * 12/2001  Eig .............................. 514/646

OTHER PUBLICATIONS

Cecil's Textbook of Medicine, Goldman et al. (eds), vol. 1, 21st edition, published 2000 by WB Saunders, pp. 258-273.*
Cecil's Textbook of Medicine, Goldman et al. (eds), vol. 2, 21st edition, published 2000 by WB Saunders, pp. 2105-2108.*
Nagao et al., "Citalopram, a Serotonin Reuptake Inhibitor, and Brain Ischemia in SHR", Brain Research Bulletin, vol. 38, No. 1, (1995), pp. 49-52.*
STN Registry File, RN 59729-32-7, "Citalopram hydrobromide", Entered STN: Nov. 16, 1984.*
Physician's Desk Reference, 46th Edition (1992), pp. 1019-1020.*
The Merck Index, 11th edition, published 1989 by Merck & Co., Inc., (NJ), pp. 3521-2, citation 3521, "Enalapril".*
Eddahibi et al., American Journal of Respiratory and Critical Care Medicine, vol. 159, No. 3 (S), 1999 p. A165 XP009013758.

* cited by examiner

Primary Examiner—Raymond J Henley, III
(74) Attorney, Agent, or Firm—Birch, Stewart, Kolasch & Birch, LLP

(57) ABSTRACT

The invention relates to the use of citalopram or a pharmaceutically acceptable salt thereof for the preparation of pharmaceutical compositions suitable for the treatment of elevated (high) blood pressure, normalization of blood pressure or the decrease of elevated blood pressure and/or prevention of elevated blood pressure.

8 Claims, No Drawings

CITALOPRAM FOR THE TREATMENT OF ELEVATED BLOOD PRESSURE

FIELD OF THE INVENTION

The present invention relates to a new use of citalopram.

TECHNICAL BACKGROUND OF THE INVENTION

It is known that 1-(3-dimethylamino-propyl)-1-(4-fluoro-phenyl)-1,3-dihydro-5-isobenzofurance-carbonitrile (INN citalopram) is a well-known antidepressive pharmaceutical active ingredient (DE 2,657,103). The optically active (S)-citalopram having also antidepressive effect is described in EP 346,066.

Several synthetic procedures are known for the preparation of citalopram (WO 98/19512 and WO 98/19513).

It is known from the information leaflet of products containing citalopram—e.g. "Celexa Side Effects Celexa Drug Interactions Citalopram-Rx List Monographs"—that in the course of treatment of depression with citalopram hypotension may occur as an undesirable side effect.

However, this does not mean that citalopram is declared as a product normalizing the blood pressure of patients suffering from hypertension. Firstly: the above mentioned reference does not relate to hypertonic patients. Secondly: it was disclosed that "although the reported cases occurred in the course of treatment carried out with CELEXA™ (citalopram), it is not necessary that said side effect was caused by" CELEXA™ ("CELEXA™" is the trademark of a product containing citalopram). Thirdly: the fact that hypertension, i.e. the opposite to hypotension, was also given as an undesired side effect, strongly supports the statement that the reference contained no unambiguous teaching for hypotension caused by citalopram. Fourthly: the undesired induction of hypotension is not a blood pressure normalizing effect because hypotension is an abnormal blood pressure per Se. For the reasons stated above, the cited reference contains no teaching or disclosure of the use of citalopram for the treatment of hypertension, normalization of blood pressure or decrease of elevated blood pressure respectively.

The aforesaid also relates to the information leaflet of a "SEROPRAM product, active ingredient CITALOPRAM", wherein the postural type of hypotension was mentioned as undesired side effect.

SUMMARY OF THE INVENTION

The object of the present invention is the development of a new use of citalopram or pharmaceutically acceptable salts thereof.

The above object is solved in a surprising way with the aid of the present invention.

The present invention relates to the use of citalopram or a pharmaceutically acceptable salt thereof for the preparation of pharmaceutical compositions suitable for the treatment of elevated (high) blood pressure, normalization of blood pressure or the decrease of elevated blood pressure and/or prevention of elevated blood pressure.

DETAILED DESCRIPTION OF THE INVENTION

The definition of the terms used in the present patent specification is the following:

The term "pharmaceutically acceptable salts" relates to salts formed with pharmaceutically acceptable inorganic or organic acids. Such salts are the hydrochloride, hydrobromide, sulfate, phosphate, nitrate, acetate, tartrate, maleate, fumarate, lactate, maleate, benzenesulfonate etc.

The term "hypertensive" relates to a blood pressure of 180/110 Hgmm or a higher value.

The term "normotensive" relates to a blood pressure of 130/80 Hgmm±10 Hgmm.

Citalopram can be used either as the racemate or in an optically active form, e.g. (S)-citalopram.

Citalopram possesses numerous advantages over known antihypertensive agents. Often the normalization of blood pressure cannot be achieved with the aid of antihypertensive agents used in clinical practice, partly because of the fluctuation of blood pressure and partly due to a decrease of blood pressure below the normal level. The disadvantages of the majority of known antihypertensive agents are the induction of insomnia, fatigue, irritation especially in the morning, disturbed concentration, problems of memory and mood, decrease of motivation. On the other hand, citalopram does not cause anxiety and affective disturbances, so much the less as the main indication thereof is just the treatment of such disturbances.

Citalopram may be excellently used for the normalization of blood pressure. It is rather frequent that in course of treatment with generally used antihypertensive agents patients who were previously normotensive or hypotensive and who have recovered from depression or anxiety disorders become hypertonic after several months or years. In such cases the substitution of the hitherto used antihypertensive agent by citalopram abolishes the affective and anxiety complaints in addition to normalizing blood pressure.

According to a preferred embodiment of the present invention citalopram or a pharmaceutically acceptable salt thereof is used for the treatment and/or prevention of unstable elevated blood pressure.

According to a further preferred embodiment of the present invention citalopram or a pharmaceutically acceptable salt thereof is used for the treatment and/or prevention of elevated blood pressure which occurs in patients with panic disorders.

Unstable hypertension is not only characteristic for the young generation of about 20 years of age. Practice has proved that unstable hypertension is present from childhood to the old age and frequently represents the first sign of panic disorder. Nevertheless, this is only an apparent observation. Extensive anamnesis explored that affective disturbances or panic disease, sometimes only one or two sporadical panic attacks, had already occurred in the medical history of elderly patients.

For the reasons stated above, citalopram is particularly suitable and preferred for the treatment of elevated blood pressure of the above type.

Unstable hypertension occurring with panic disorders may turn into serious fixed hypertension over a period of time. It has been surprisingly found that citalopram is useful in the treatment of the above disease i.e. in the normalization of unstable blood pressure simultaneously with all symptoms of panic disease, including panic attacks, anticipatory anxiety, agoraphobia, and in half of the cases panic disorders associated with depression.

In case of the above diseases the necessity of the administration of citalopram is indicated by the occurrence of hypertension.

According to a further preferable embodiment of the present invention citalopram or a pharmaceutically acceptable salt thereof is used for the treatment and/or prevention of essential elevated blood pressure.

Essential hypertension is presented in 80% of the patients suffering from elevated blood pressure. It is supposed that the term "essential" means a complete response to citalopram (responsiveness) in the majority of the cases (relevant hypertonic sub-group).

According to a further preferred embodiment of the present invention citalopram of a pharmaceutically acceptable salt thereof is used for the prevention and/or treatment of stroke.

It is known that the great majority of patients suffering from stroke belongs to hypertonic patients. Stroke is a serious harmful factor world-wide. About 55 million people suffer from unstable hypertension all over the world but the number of patients having fixed hypertension originated from unstable hypertension is several times higher.

In Hungary 170,000 patients younger than 40 years suffered from stroke and died in 1979.

Citalopram can be used in the long term treatment of hypertension either in monotherapy or in combination with other antihypertensive agents.

In case of mild or moderate hyperthonia citalopram improves the blood pressure already in monotherapy. In more severe cases citalopram exhibits a considerable antihypertensive effect as well, i.e. a further antihypertensive agent can be administered in a significantly lower dose. Accordingly in every day's medical practice citalopram provides the normalization of blood pressure.

According to a further preferred embodiment of the present invention pharmaceutical composition are prepared which contain citalopram or a pharmaceutically acceptable salt thereof together with a further antihypertensive agent. For this purpose e.g. the following antihypertensive agents can be used: an antihypertensive agent having central effect, preferably methyldopa, clonidine, guanfacine, guanabenz; a β-blocker, preferably acebutolol, atenolol, betaxolol, bisoprolol, carteolol, propranolol, metoprolol, nadolol, penbutolol, pindolol, timolol, bucindolol, labetalol, carvedilol, nevibolol; an α-blocker, preferably prazosin, terazosin, doxazosin, trimazosin, phenoxybenzamide, phentolamine; a direct vasodilator, preferably hydralazine, minoxidil, diazoxide, fenoldopam; a calcium channel blocker, preferably verapramil, diltiazem, nifedipine, nimodipine, felodipine, nicarpidine, israpidine, amlodipine, nisolpidine, lacidipine; an ACE-inhibitor, preferably captopril, enalapril, lisinopril, quinapril, ramipiril, benazepril, fosinopril, moexipril, quinapril, perindopril, ramipril, trandolapril; an angiotensin II receptor antagonist, preferably losartan, candesartan, irbesartan, valsartan, telmisartan, eprosartan; an imidazolin receptor agonist, preferably moxonidine, rilmenidine. The above enumeration serves only the purpose of exemplification but not of limitation.

The antihypertensive pharmaceutical compositions of the present invention preferably contain in addition to citalopram or a pharmaceutically acceptable salt thereof at least one pharmaceutically acceptable inert carrier and/or auxiliary agent.

The citalopram containing antihypertensive pharmaceutical composition prepared according to the present invention can be administered preferably orally or parenterally. For oral administration e.g. tablets, coated tablets, hard or soft gelatine capsules dragees, solutions, suspensions or emulsions can be used. Parenteral pharmaceutical compositions may be e.g. in the form of intravenous, intramuscular or intraperitoneal injectable solutions.

Solid pharmaceutical compositions for oral administration contain in addition to the active ingredient usual pharmaceutical excipients. For this purpose e.g. binders (e.g. gelatine, sorbitol and/or polyvinyl pyrrolidone), carriers (e.g. lactose, glycose, starch and/or calcium phosphate), tabletting auxiliary agents (e.g. magnesium stearate, talc and/or silicium dioxide) and/or wetting agents (e.g. sodium lauryl sulfate) can be used.

Liquid pharmaceutical compositions for oral administration can be e.g. solutions, suspensions or emulsions. Such compositions can contain suspending agents (e.g. gelatine and/or carboxy-methyl cellulose), emulsifying agents (e.g. sorbitane monoolate), solvents (e.g. water, oils, glycerol, propylene glycol and/or ethanol) and/or preservatives (e.g. methyl-p-hydroxy-benzoate).

Parenterally administrable pharmaceutical compositions may be preferably sterile solutions of the active ingredient formed with water or an isotonic sodium chloride solution.

The daily dose of citalopram as antihypertensive agent is preferably between about 0.01 mg/kg bodyweight and about 2 mg/kg bodyweight, particularly between about 0.07 mg/kg bodyweight and 1 mg/kg bodyweight. The starting dose of citalopram is preferably about 5 mg/day and thereafter the stable dose is about 20–60 mg/day for several months. The dose of (S)-citalopram is approximately the half of the above values.

In case of oral treatment the administration of citalopram in the form of an infusion may be necessary (starting "overloading" dose).

According to a further aspect of the present invention there is provided a process for the treatment of elevated (high) blood pressure, normalization of blood pressure, or the decrease of elevated blood pressure and/or the prevention of elevated blood pressure which comprises administering to the patient in need of such treatment a pharmaceutically efficient amount of citalopram and/or a pharmaceutically acceptable salt thereof.

According to a preferred embodiment of the invention said method of treatment is used for treating a patient suffering from unstable elevated blood pressure.

According to a further preferred embodiment of the invention said method of treatment is used for treating a patient suffering from unstable blood pressure which occurs together with panic disorders.

According to a further preferred embodiment of the invention said method of treatment is used for treating a patient suffering from essential elevated blood pressure.

According to a further preferred embodiment of the invention said method of treatment is used for treating a patient suffering from or exposed to stroke.

The antihypertensive effect of citalopram is demonstrated by the following tests.

I. Study

Verification of the Antihypertensive Effect of Citalopram 254 patients participated in the study. All patients were hypertonic. In this group of hypertonics there were 120 patients suffering from panic disorder and agoraphobia, 70 patients suffering from panic disorder with agoraphobia and with depression, and 64 patients suffering from panic disorder with agoraphobia and with social phobia and/or with obsessive compulsive disorder (OCD).

The patients received citalopram in a dose of 5 mg/day on the first week, 10 mg/day on the second week and 20 mg/day on the third and fourth week.

After the 4 weeks treatment there was a complete recovery of 170 patients (67%). Theses patients became normotensive and the symptoms of anxiety and affective disorders fully disappeared.

The citalopram treatment of the remaining 84 patients was continued with a weekly oral dosage of 20 mg/day. From said 84 individuals 64 patients were additionally treated orally with metoprolol for 3 weeks in a dose of 2×50 mg/day and 20 patients received captopril in a dose of 2×12.5 mg/day. After 6 weeks complete recovery was experienced, the patients became normotensive and the symptoms of anxiety and depression fully disappeared.

As a result of the treatment the patients suffering from unstable hypertension recovered.

The above results show unambiguously that citalopram restores elevated blood pressure, normalizes unstable high blood pressure, recovers the normotensive state of patients and additionally cures the various symptoms of anxiety and depression of patients suffering from high blood pressure.

II. Study

Study of Patients Suffering from Unstable High Blood Pressure, Previously Treated with Antidepressants In the study 13 patients having unstable high blood pressure were used who suffered from different anxiety disorders and depression.

Out of these patients 3 suffered from panic disorder, 1 from obsessive compulsive disorder and 9 from panic disorder with depression. On the beginning of treatment with the following antidepressants the patients were normotensive.

The patients were treated orally with 40 mg/day of paroxetine, or 100 mg/day of sertraline, or 20 mg/day of fluoxetine, or 150 mg/day of fluvoxamine. After 6 months 60% of the patients and after a period of 12–30 months 40% of the patients became hypertensive beside the normalization of their psychiatric state.

Thereafter the above mentioned antidepressants were substituted with citalopram. The oral dose of citalopram was 5 mg/day on the first week, 10 mg/day on the second week and 20 mg/day on the third week. Surprisingly at the end of the treatment the patients became normotensive.

The above experimental results prove that contrary to the referent antidepressive agents citalopram is capable of normalizing the unstable elevated blood pressure occurred beside anxiety and affective disorders. It clearly follows from the above surprising results that it is highly advisable to start the treatment of anxious and depressive patients suffering from high blood pressure with citalopram.

III. Study

Study of Patients Suffering from High Blood Pressure But without Anxiety or Depressions In the test 102 hypertensive patients participated who complained of the following symptoms: attack like headache, dizziness, trembling, tremor, sweating, fear of death, sensation of heat and cold, and gastrointestinal complaints. The patients thought that their complaints were the consequence of panic attacks, but this was not supported by their psychiatric anamnesis in an unambiguous manner.

The patients were orally treated with citalopram in a dose of 5 mg/day on the first week, 10 mg/day on the second week and 20 mg/day on the third week. After the three weeks' treatment 47 patients (46%) recovered and became normotensive.

From the 55 non-responder patients 40 individuals (39%) received betaloc in an oral dose of 100 mg/day and 15 patients (15%) received captopril in a dose of 2×12.5 mg/day, in addition to the administration of 20 mg/day of citalopram. After a six weeks treatment complete recovery was experienced and the patients became normotensive.

The above results duly show that citalopram normalizes high blood pressure and abolishes panic-like symptoms induced by high blood pressure too. Also in such cases it is highly advisable to start the treatment with citalopram.

Thus citalopram is suitable for the treatment of high blood pressure occurring with non-affective disorders both in monotherapy and in combinations.

IV. Study

Study of Patients Suffering from Panic Disorders and/or Affective Disturbances Whose Case Report Contains at Least One Hypertensive Episode In the study 25 patients suffering from panic disorders and/or affective disturbances participated. These patients showed hypertensive episode(s) in their medical history at least once. The patients received orally citalopram in a dose of 5 mg/day on the first week, 10 mg/day on the second week and 20 mg/day on the third week. The patients responded completely to the treatment, the syndromes of panic and affective disorders completely ceased and blood pressure remained in the normal range.

The above test results show that citalopram is an excellent choice in patients suffering from panic disorder and/or affective disturbances whose case record contains at least one hypertensive episode. Namely the hypertonic episode can be considered to be a biological marker of the necessity of the use of citalopram.

V. Study

Study of Depressed Patients Who Have Parents Suffering from High Blood Pressure or Stroke In the study patients suffering from anxiety or affective disorders were used who had at least one parent being hypertensive or punished by stroke. It has been found that on treating such patients with citalopram in the oral dose disclosed above blood pressure remained normal for a longer period of time and additionally the symptoms of anxiety and depression disappeared. Treatment performed by using any other antidepressant failed to produce complete responsiveness. Thus the use of citalopram in the treatment of the above group of patients is highly preferred.

What I claim is:

1. A method for normalizing the blood pressure of a patient who is hypotensive or hypertensive whereby the patient becomes normotensive which consists of
    administering to a patient in need thereof a pharmaceutically efficient amount of citalopram and/or a pharmaceutically acceptable salt thereof.
2. The method according to claim 1, wherein the patient suffers from unstable hypertension.

3. The method according to claim 1, wherein the patient suffers from unstable blood pressure which occurs in patients with panic disorders.

4. The method according to claim 1, wherein the patient suffers from essential hypertension.

5. The method according to claim 1, wherein the citalopram is in racemic form.

6. The method according to claim 1, wherein the citalopram is (S)-citalopram.

7. A method for normalizing the blood pressure of a patient who is hypotensive or hypertensive whereby the patient becomes normotensive which comprises administering to a patient in need thereof a pharmaceutically efficient amount of citalopram and/or a pharmaceutically acceptable salt thereof, wherein the patient suffers from or is exposed to stroke.

8. A method for normalizing the blood pressure of a patient who is hypotensive or hypertensive whereby the patient becomes normotensive which consists of
administering to a patient in need of thereof a pharmaceutical composition comprising citalopram and/or a pharmaceutically acceptable salt thereof and at least one pharmaceutically acceptable inert carrier.

* * * * *